US008278091B2

(12) United States Patent
Rutter et al.

(10) Patent No.: US 8,278,091 B2
(45) Date of Patent: Oct. 2, 2012

(54) ASSAY DEVICE

(75) Inventors: Paul Rutter, Hatton Park (GB); Chris Jones, Gloucester (GB); Andrew Ledgeway, Fareham (GB); James Gani, Bedford (GB); Bryan Tissington, Cambridgeshire (GB)

(73) Assignee: Alere Switzerland GmbH, Zug (CH)

( * ) Notice: Subject to any disclaimer, the term of this patent is extended or adjusted under 35 U.S.C. 154(b) by 1075 days.

(21) Appl. No.: 11/958,912

(22) Filed: Dec. 18, 2007

(65) Prior Publication Data

US 2010/0255609 A1 Oct. 7, 2010

(30) Foreign Application Priority Data

Dec. 19, 2006 (GB) .................................. 0625309.0

(51) Int. Cl.
*G01N 33/543* (2006.01)

(52) U.S. Cl. ..................... 435/287.2; 422/401; 422/405; 422/406; 422/420; 422/430; 435/287.6; 435/287.7; 435/287.9; 435/288.2; 435/288.5; 435/810; 435/970; 436/518; 436/810

(58) Field of Classification Search ........................ None
See application file for complete search history.

(56) References Cited

U.S. PATENT DOCUMENTS 3,713,780 A * 1/1973 Shapiro .......................... 422/413
4,657,869 A * 4/1987 Richards et al. ........... 435/287.6
4,965,047 A * 10/1990 Hammond ..................... 422/413
5,415,994 A * 5/1995 Imrich et al. ....................... 435/5
6,017,494 A * 1/2000 Ashihara et al. .............. 422/412
6,375,896 B1 * 4/2002 Wuske et al. ................. 422/411
6,468,474 B2 * 10/2002 Bachand et al. .............. 422/411
7,713,475 B2 * 5/2010 Gould et al. .................. 422/413

* cited by examiner

*Primary Examiner* — Chris L Chin
(74) *Attorney, Agent, or Firm* — Foley Hoag LLP

(57) ABSTRACT

Provided is an assay device and kit for detecting the presence or amount of an analyte of interest.

6 Claims, 11 Drawing Sheets

ASSAY DEVICE

CROSS-REFERENCE TO RELATED APPLICATION

This application claims the benefit of GB Application No. 0625309.0, filed Dec. 19, 2006 the contents of which are hereby incorporated by this reference in their entirety.

BACKGROUND

Simple disposable assay devices for the detection of an analyte in a liquid sample are well known. EP291194 discloses such a device comprising a porous flow through carrier wherein a labelled binding reagent is caused to interact with a liquid sample of interest and flow through the device. Detection of the labelled binding reagent at a downstream detection zone provides an indication of the amount or presence of analyte in the sample. Such devices require the sample to be in a liquid form in order to be able to pass through a porous matrix. Thus liquid samples such as urine may be used directly in such a device without further treatment. However, low viscosity, solid or semi-solid samples such as sperm or saliva, or samples taken from a throat swab may need to be diluted prior to use. Furthermore, the sample may need to be pre-treated with a fluid in order to expose the analyte of interest.

US20060024843 discloses a lateral flow assay device comprising an assay test strip in combination with a sample containing unit for detection of a sample of interest. The sample containing unit provides the ability to extract, dilute, or treat the sample in any other way before introducing it onto the test-strip. For this purpose, the unit may contain an extracting or diluting solution. Following a suitable incubation period, a seal separating the liquid from the test-strip is broken by rotation of the sample containing unit by the user.

U.S. Pat. No. 4,654,127 discloses a single use assay device comprising a fluid container comprising a test sample chamber and a separate chamber containing a calibrant fluid provided within first and second rupturable seal means wherein rupture of the seal means allows the calibrant fluid to flow to the assay means.

Many liquid containers include a liquid tight openable seal which may be opened to allow access to the liquid contained therein. Examples of such containers include drink cartons, cosmetics containers, pharmaceuticals containers, etc. The liquid-tight seal serves a number of useful functions such as retaining the liquid within the container and preventing or minimising evaporation of liquid. The seal may be removed by peeling it away at least partially to reveal the contents of the container. The seal may for example be in the form of a screw cap to be unscrewed by the user, or to be pressed down into the container in order to open it. Alternatively, as in the case of some drinks containers, the seal may be puncturable and punctured by use of a sharp implement such as a pointed straw in order to access the liquid contained therein.

U.S. Pat. No. 5,079,141 discloses a pre-filled and pre-sealed apparatus for carrying out chemical, particularly immunochemical, analyses. The apparatus comprises a test base containing therein wells, into which are introduced all the reagents necessary for performing the assay reaction in question. The apparatus further comprises a reagent stick having at one end a sharp reactive point onto which a sample to be assayed can be adsorbed. The base and wells are covered with an impervious foil layer which can easily be pierced with the sharp reactive end of the testing stick included in the apparatus.

Such fluid containers designed to be directly punctured by an item or sampling device typically have seals of low elasticity, which are punctured by applying mechanical force to insert a sampling device through the seal and into the liquid container. In order to minimise evaporation the seals may be a thick metal foil. However there are a number of drawbacks with this arrangement. For example, the user of the device may not have sufficient strength to puncture the seal due to the high puncture force required to force the sampling device through it. Alternatively, the user may thrust the sampling device into the test apparatus using inappropriately excessive force, thereby damaging the apparatus and/or device and/or causing liquid to be ejected from the container. In order to reduce the force required to pierce the foil, the foil may be made to be very thin or contain perforations or hairline grooves. However, this increases the chance that liquid may evaporate from the container, due to presence of pin-holes or that the seal is less robust. Direct insertion of the item through the seal also requires that the item to be inserted is sharp enough to pierce the seal. It is not always convenient to provide a sharp item, for example in the case wherein the item is a sampling device for insertion into a bodily orifice.

SUMMARY

Accordingly, provided is an assay device comprising a sealed liquid container containing a liquid which is suitable for use with a sampling device wherein the sampling device may be easily and conveniently inserted into the liquid container. The assay device is suitable for determining the presence or amount of an analyte in a sample wherein the user is required to carry out a minimal number of steps in operating the assay device.

In certain embodiments, the assay device comprises a fluid seal opening means. In other embodiments, the assay device comprises a liquid container as well as to an opening means and to a liquid container suitable for use with an assay device.

Further objectives and advantages of the present invention will become apparent as the description proceeds. To gain a full appreciation of the scope of the present invention, it will be further recognized that various aspects of the present invention can be combined to make desirable embodiments of the invention.

DETAILED DESCRIPTION

Figure 1:
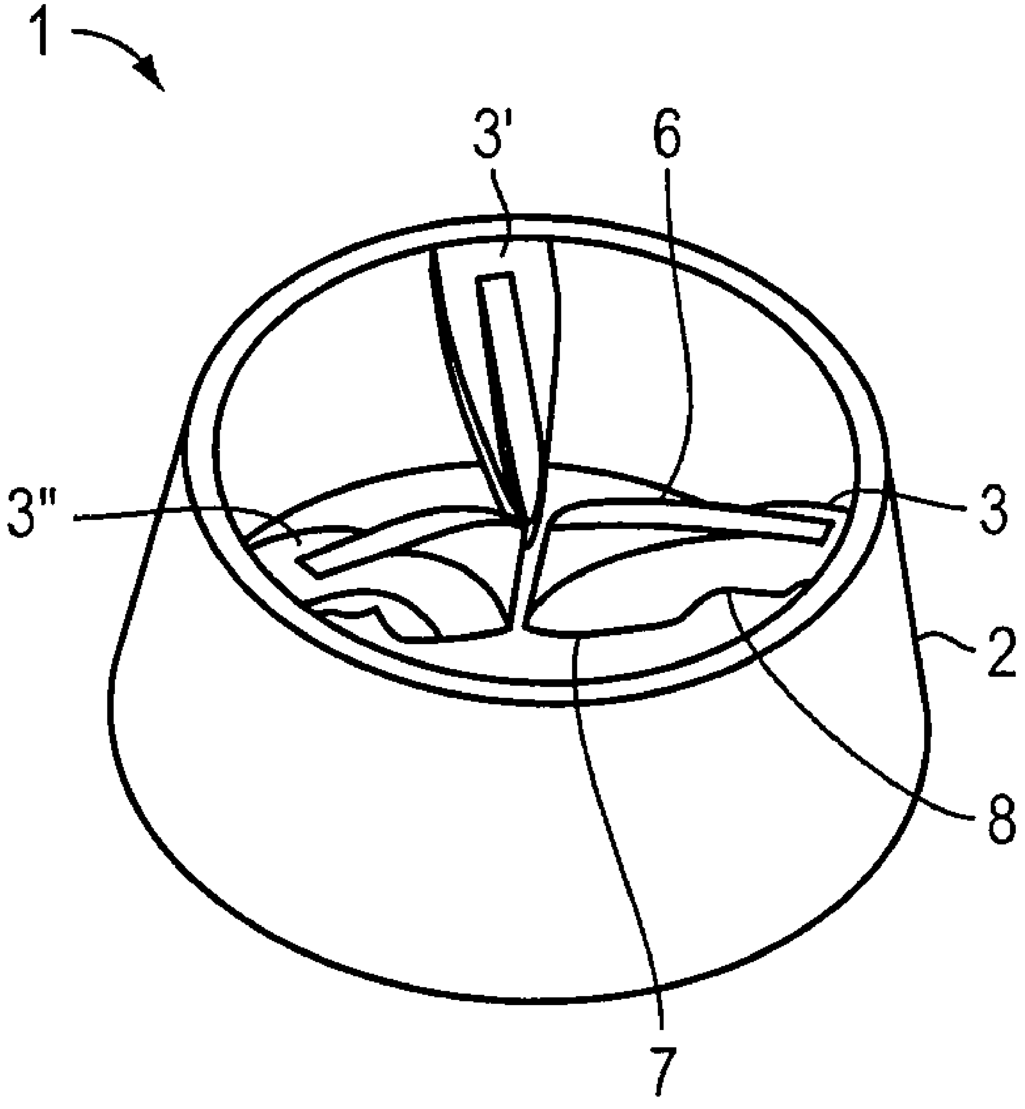
FIG. 1 shows an elevated view of a puncturing device of the present invention.

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The articles "a" and "an" are used herein to refer to one or to more than one (i.e., to at least one) of the grammatical object of the article. By way of example, "an element" means one element or more than one element.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including, for example, any of the classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "binding reagent" refers to a member of a binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be an binding pair member for the immune complex.

The terms "comprise" and "comprising" is used in the inclusive, open sense, meaning that additional elements may be included.

The term "including" is used herein to mean "including but not limited to". "Including" and "including but not limited to" are used interchangeably.

"Label" when used in the context of a labelled binding reagent, refers to any substance which is capable of producing a signal that is detectable by visual or instrumental means. Various labels suitable for use in the present invention include labels which produce signals through either chemical or physical means. Such labels can include enzymes and substrates, chromogens, catalysts, fluorescent compounds, chemiluminescent compounds, electroactive species and radioactive labels. Other suitable labels include colloidal metallic particles such as gold, colloidal non-metallic particles such as selenium or tellurium, dyed or colored particles such as a dyed polymer. The analyte itself may be inherently capable of producing a detectable signal.

The term "openable seal" refers to a seal which is capable of being either partially or fully removed or opened or punctured in order to access the liquid within the container. The seal may be puncturable. The seal may be a valve which is capable of being actuated to move from a closed position to an open position.

The term "opening means" refers to a means which is capable of opening the first openable seal either directly or indirectly. The opening means may be a switch or other mechanism which serves to open the seal or which serves to puncture the seal. In a preferred embodiment, the opening means is a puncturing means and the first openable seal is puncturable. The second openable seal may be puncturable. The liquid container may comprise an opening means capable of opening the second seal. The opening means may be an additional opening means to the first opening means.

The term "sample" refers to any specimen, preferably a fluid, potentially containing an analyte.

The term "sample mixing liquid" refers to a liquid that interacts with the sample. Interaction of the liquid with the sample may result in a dilution, a reaction, a binding event or a suspension.

In a first aspect, the invention provides an assay device for determining the presence and/or amount of an analyte of interest in a sample, the assay device comprising:

a sample receiving liquid container for containing a liquid and adapted to receive the sample into said liquid, the liquid container comprising a first openable liquid seal and a second openable liquid seal;

an opening means capable of opening the first liquid seal; and an assay means for determining the presence and/or amount of an analyte of interest in the sample.

The liquid container contains a liquid which is sealed within the container by the first and second liquid seals. The liquid may be aqueous in nature. Although the present invention is described herein with reference to liquids, it will be appreciated that the present invention is equally applicable for fluids.

The first seal seals a first opening of the liquid container and may be provided in proximity to the opening means and the second seal seals a second opening of the liquid container which fluidically separates the liquid container from the assay means. The first seal may be provided at a location distal from the assay means and the second seal provided at a location proximal to the assay means. The first and second seals may be provided at opposite ends of the container. The first seal may be located at an upper end of the liquid container and the second seal may be located at a lower end of the liquid container.

The liquid container may comprise a single liquid chamber. Alternatively, the liquid container may comprise a plurality of liquid chambers each containing a liquid or wherein one of them contains a liquid sensitive reagent and the remaining chambers contain a liquid. Where a plurality of liquid chambers are provided, they may be separated from each other by one or more openable liquid seals, such that insertion of a sampling device into the liquid container results in the interaction of the sampling device with the liquid chambers, resulting in either mixing of the liquid contained in the respective liquid chambers or mixing of a liquid in one liquid chamber with a liquid sensitive reagent in another liquid chamber.

In the case where the first openable seal is a puncturable seal and the opening means is a puncture means, provision of an assay device comprising a puncture means allows a user to simply and easily insert an item into the liquid container via a puncturable seal, without the item itself directly puncturing the puncturable seal. Thus the need to use excessive force in order to contact the item with the fluid provided within the sealed fluid container is minimised. The puncturing device also allows the user to employ an item which is relatively blunt as the item itself does not directly open the openable seal. Furthermore, the puncturing device allows for a relatively thick puncturable material to be used, which provides an optimal protection against evaporation of liquid from the liquid chamber.

The first and/or second seals may be chosen from a material having low fluid permeability such as a metal, alloy or polymer layer. The layer may have a thickness in the range of from about 15 to about 50 microns. A layer less than about 15 microns tends to have pin-holes and a layer greater than about 50 microns tends to require too high a puncture force in order to puncture the seal. Preferably, in the case of a puncturable seal, the thickness of the seal may range from between about 20 to about 30 microns. The metal layer may be aluminium foil. The layer may further comprise a bondable backing layer such as a lacquer or a laminate to enable the layer to be bonded to the liquid container.

The assay device may comprise one or more reagents appropriate for the assay in question. Examples of reagents may be chosen from, but not limited to, a binding reagent capable of binding to an analyte of interest, an enzyme, a surfactant, a buffer, an extraction reagent, a salt, a precipitation reagent, a viscosity modifying reagent and a lysing reagent. The binding reagent may be labelled with a detectable label. The one or more reagents may be provided within the liquid container and/or within the assay means. The reagents may be provided in the dry state or in the wet state.

The assay means may comprise a liquid pathway such as a capillary channel, a microfluidic pathway, or a porous flow through carrier such as a lateral flow porous carrier. The liquid pathway may lead to a detection chamber or zone. The porous flow through carrier may comprise one or a plurality of porous carrier materials which in use are fluidically connected. The plurality of porous carrier materials may be the same or different. The plurality of porous carriers may at least partially overlap one another in a linear or stacked arrangement. The assay means may comprise a lateral flow carrier material, such as are described, for example, in EP291194. The assay means may comprise a plurality of liquid pathways each defining a separate flow path for the detection of an analyte. The analyte may be the same or different. Where a plurality of liquid pathways are provided they may have a common sample receiving portion such that liquid from the liquid container is able to flow to each flow channel.

In one embodiment, the assay means comprises a flow through carrier wherein a carrier material of a first porosity is in fluidic connection with a carrier material of a second porosity smaller than that of the first carrier material such that a binding or reaction product of the assay reaction may be retained at the second carrier material and detected in order to determine the presence or extent of an analyte in the sample.

The assay means may comprise one or more reagents appropriate for the assay in question. The one or more reagents may be chosen from a binding agent capable of binding to the analyte of interest, a reagent that is able to react with the analyte of interest, such as an enzyme, a reagent that is able to interact or otherwise react with the products of any interaction between the analyte of interest and a further reagent. The assay means may comprise a detection zone which is capable of detecting a product of the interaction or reaction of the analyte of interest and one or more reagents.

In one embodiment, the assay means comprises a detection zone which is capable of immobilising a labelled binding reagent for an analyte of interest. The detection zone may comprise an immobilised binding reagent. In a further embodiment, the assay means comprises a detection zone capable of immobilising a chemical or biochemical product formed from reaction between at least a reagent and the analyte of interest. Detection or observation of an immobilised product at the detection zone provides an indication of the presence and/or amount of an analyte present in the sample.

In a further embodiment, the assay means comprises an enzyme for the analyte of interest. The assay means may further comprise an electron mediator for the enzyme or a colour developing reagent and/or a precipitation reagent.

According to one embodiment, the assay means is an immunoassay means and/or an enzyme assay means.

The analyte of interest to be determined by the assay device may be of a biological, industrial or environmental nature. The analyte may be of a mammalian, especially of a human origin. The analyte of interest may be any of significance including toxins, organic compounds, proteins, peptides, microorganisms, bacteria, viruses, amino acids, nucleic acids, carbohydrates, hormones, steroids, vitamins and drugs. The analyte may be one which requires a liquid pre-treatment step before being exposed to an assay means. The liquid treatment step may comprise one or more of, but not limited to, a dilution, a liquid suspension, an extraction, a binding reaction, a biochemical reaction, a chemical reaction, a buffering, a treatment with a surfactant. The pre-treatment step may be carried out by introducing the analyte of interest into the liquid container and allowing it to interact with the liquid container therein. The liquid container may comprise one or more reagents which enable a pre-treatment step to be carried out. In particular, analytes of interest include *Streptococcus A, Candida* organisms and bacterial vaginosis organisms.

The sample can be derived from any source, such as a physiological liquid, including blood, serum, plasma, saliva, sputum, ocular lens liquid, sweat, urine, milk, ascites liquid, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions, amniotic liquid, and the like.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

The assay device may further comprise a housing means which serves to house one or more components of the device, such as the assay means. The assay device may further comprise a detection means for detecting a product of the assay. The detection means may be chosen from any suitable means, such as an optical detection means, an electrochemical detection means, a mass detecting means and a frequency detecting means. The assay device may further comprise one or more means such as a display means for displaying the result of the assay; a memory means for storing the results of an assay as well as other information such as patient identification, date and time; a computing means, a signal transduction means and a power source.

The assay device according to the first aspect is suitable for use with a sampling device such that in use, the sampling device contacts the opening means resulting in the opening of the first openable liquid seal such that the sampling means is able to be inserted into the liquid container. Following interaction between the sample and the liquid in the liquid container, the second openable seal may be opened to allow the liquid to flow from the liquid container to the assay means. The second openable seal may be opened directly by the sampling device. Alternatively, the second seal may be opened by a second opening means. The second seal may be punctured by a puncturing means provided within the liquid container.

The assay device may further comprise a sampling device capable of transferring a sample to the liquid container of the assay device. The sampling device may be any suitable item such as an absorbent or porous material chosen for example from a sponge or swab. Alternatively it may be a non-absorbent material such as a spatula. The sampling device may be adapted to fit with the assay device, and/or vice-versa, thereby forming an integral part of the assay device.

The sampling device may be any device designed to take a solid, semi-solid or liquid sample from any source. For example, the sampling device may be adapted to take a bodily sample from an animal subject, such as a mammal. In preferred embodiments, the sampling device is adapted to take a bodily sample from a human subject. Alternatively, the sampling device may be adapted to take a sample from a plant, from a body of liquid, from the soil, or from other sources.

The sampling device may comprise a head portion specifically adapted to enhance the efficiency with which the device collects a sample. For example, the head portion of a sampling device may be formed in a particular shape which increases the likelihood of the sampling device collecting sample material from a source. For example, the head portion may form an elongate shaft, a spiral shape, a conical shape, or other shapes. The head portion may additionally comprise radially protruding structures for capturing sample material. For example, the head portion may comprise radiating bristles, or resilient radiating protrusions, or may comprise a porous material such as a sponge or a flocked material. Other adaptations of the sampling device will be readily apparent to the person skilled in the art. For example, the shape of the sampling device may be adapted to minimise discomfort to a subject when a sample is taken from a subject (e.g. from a bodily orifice).

The sampling device may further comprise an elongate shaft attached to the head portion. The diameter of the shaft may be less than the diameter of the head portion. The sampling device may also comprise a handle portion for the user to hold whilst taking a sample. The handle portion may be adapted to provide the user with greater ease of using the sampling device. For example, the handle portion may comprise protrusions which increase the frictional force between the user's hand and the handle, to prevent the sampling device from slipping whilst a sample is taken. Thus, the handle portion may be ribbed, or composed of a material which increases the frictional force between the handle and the user's hand.

The assay device may also comprise a means such as a hollow neck portion capable of receiving a sampling device. The means may guide the sampling device towards the opening means capable of opening the first liquid seal of the liquid container. The receiving means may surround the liquid container and extend vertically above the liquid container. The neck portion may include one or more projections, such as fin portions which serve to guide the sampling device to the opening means. The projections may extend perpendicularly into the bore of the neck portion and extending longitudinally along at least part of the neck portion. The distance which the projections extend into the bore of the neck portion may be adapted so that the sampling device contacts the edge of the projections and is guided towards the centre of the first liquid seal and opening means capable of opening the first liquid seal. Preferably, the surface area of the edge of the projections is minimised so that there is minimal contact between the sampling device and the projections. This reduces the chances of sample material contacting the side walls of the neck portion and being deposited thereon and therefore increases the chance that more sample material is transferred into the liquid container of the assay device.

The assay device is intended for use by an individual user or by a medical professional. The simplicity of use of the assay device makes the device particularly suitable for home use.

In a second aspect, the invention provides a method of determining the presence and/or amount of an analyte of interest in a sample, comprising the steps of:

contacting a sampling device providing a sample with the assay device of the first aspect, wherein contacting the opening means of the assay device with the sampling device results in the opening of the first openable liquid seal of the liquid container;

inserting the sampling device into the liquid container containing a liquid;

opening the second openable liquid seal; and allowing the liquid to flow from the container to the assay means to be assayed for the analyte of interest.

The assay means may be integral with the fluid container and/or the opening means wherein the assay means, the container and the opening means together comprise an assay device.

The results of the assay may thereafter be visually read to determine the presence or amount of the analyte of interest.

The sampling device may reside for a period of time in the liquid container to allow time for any interaction between the sampling device and liquid to take place. The period of time may be any and typically range from less than about 1 second to about 20 minutes.

The sampling device may be agitated in the container to enhance mixing or transfer of the sample with the liquid.

According to one embodiment, in use, the user contacts the sampling device with the opening means and inserts the sampled device vertically or near vertically into the fluid container and thereafter continues the downward motion of the sampling device which results in the puncturing of the second fluid seal. As such, the user is merely required to carry out a single step in order to assay a sample after having provided the sample with the sampling device.

In a third aspect, the invention provides an assay kit comprising the assay device according to the first aspect in combination with one or more sampling devices.

The sampling device may be any suitable device such as a spatula, spoon or foam pad. In a particular embodiment, the sampling device is a swab.

A further component of the assay device may include an assay control means for determining whether a sample has successfully been applied to the assay device and/or that the assay device is functioning correctly.

Assay devices such as those disclosed by EP291194 disclose an assay control means which indicates that a fluid sample has been added to the assay device. According to an example, the control means comprises an immobilised binding reagent capable of binding a mobilizable labelled binding reagent wherein the immobilised binding reagent is provided in a zone downstream from a detection zone. Detection of immobilised labelled binding reagent at the control zone indicates that the labelled binding reagent has been resuspended and transported by the liquid sample past the detection zone to the control zone. However, a drawback of such an assay control means for an assay wherein the sample to be assayed is combined firstly with a fluid and subsequently assayed, is that the assay device is only able to indicate that a liquid sample has been applied to it and not whether a sample has been added to it. Thus a user would potentially be able to apply an unsampled sampling device to a fluid, allow the fluid to be assayed and provide a positive indication that the assay has been carried out. For assay devices which may be used by untrained personnel, such as by someone in a home-setting, there is a requirement to provide a more intelligent assay control means.

Thus, the invention provides in a fourth aspect, an assay device for determining the presence and/or amount of an analyte of interest in a sample, the assay device comprising:

a liquid container capable of containing a liquid; and an assay means for assaying the presence and/or amount of an analyte of interest in the sample;

wherein the assay means further comprises an origin specific assay control means.

In a fifth aspect, the invention provides a method of determining the presence and/or amount of an analyte of interest in a sample, comprising the steps of:

mixing a sample of interest with a fluid to form a fluid mixture;

applying the fluid mixture to an assay means and carrying out an assay for an analyte of interest, wherein the assay means comprises an origin specific assay control means.

The assay device may comprise a control reagent that is specific to a species that is prevalent in the origin of sampling. The origin of sampling may for example be from an animal, such as a human. Thus the control reagent may be an anti-human antibody to a species which is prevalent in a human. The species may be an immunoglobulin chosen from IgA, IgD, IgE, IgG, and IgM, including the four sub-types of IgG and two sub-types of IgA present in humans. For example IgA can be found in areas containing mucus (e.g. in the gut, in the respiratory tract or in the urogenital tract), IgE binds to allergens and triggers histamine release from mast cells (the underlying mechanism of allergy) and IgG (in its four forms) provides the majority of antibody-based immunity against invading pathogens. The binding reagent may comprise anti-human IgG or anti-human IgA antibody. The binding reagent may be immobilised at a control zone provided downstream from or at a detection zone. The assay means may comprise a liquid pathway in accordance with the first aspect of the invention. In a preferred embodiment, the assay means is a lateral flow immunoassay means.

In a sixth aspect, the present invention provides a puncturing device, comprising:

a member defining an aperture;

one or more puncturing elements, each puncturing element comprising a first end attached to the member and a second end extending into the aperture, the second end being movable in relation to the member and being capable of puncturing a puncturable material.

In use, an item may be inserted through the aperture of the puncturing device, contacting one, more or all of the puncturing elements as the item advances through the aperture. The item causes the one or more puncturing elements to move in generally the same direction as the item passes when the item passes through the aperture. The movement of the puncturing elements causes the second end of the puncturing elements to contact and puncture a puncturable material which may be positioned beyond the second end of each puncturing element.

Each puncturing element has a first end that is preferably attached to the inner surface of the member (the surface facing the aperture), although it may alternatively be attached to the outer surface of the member (any surface facing away from the aperture). Each puncturing element also has a second end which extends into the aperture, and which is capable of puncturing a puncturable material.

The one or more puncturing elements may be attached to the member at the first end thereof by any suitable means which allows movement of the second end. The second end may be movable between a first position, and a second position in which, in use, a puncturable material is punctured. It is preferred if movement of the second end between the first and second positions is caused by a force applied through the aperture, e.g. by an item inserted through the aperture. After this force is released, the second end may return to the first position.

The one or more puncturing elements may be attached to the member by a hinge, and may be maintained in the first position by a resilient means. For example, the puncturing elements may be maintained in the first position by a spring mechanism. Force applied to the puncturing elements by an item inserted through the aperture may move the puncturing elements into the second position. The movement of the puncturing elements may therefore be a pivoting movement around the point of attachment of each puncturing element to the member. Thus, the second end of each puncturing element may rotate around the point of attachment of the puncturing element to the member so that the second end of the puncturing element advances in an arcing motion both towards the puncturable material and towards the sides of the member.

The continued arcing movement of the puncturing elements as the puncturable material is punctured and as the item is further inserted through the aperture of the puncturing device removes the puncturable material from the path of the item as the item is progressively inserted through the puncturing device. Therefore, contact between the item and the puncturable material is minimised as the item is inserted through the puncturing device and into a container having the puncturable material thereon. The puncturing elements may form an integral part of the member. The member, the puncturing elements and/or the hinges may be formed of the same material or of different materials. The hinge may be formed by providing a thin section of material between the puncturing elements and the member. For example, certain materials such as (by way of a non-limiting example) polyethylene are flexible when formed with a thin cross section, and are rigid when formed with a large cross section. Other materials with such a property are known to those skilled in the art. The resilience of the material may be sufficient to maintain the puncturing elements in the first position, though the elements may be urged to move to the second position by an item inserted through the aperture.

The level of resistance preventing the puncturing elements from moving from the first to the second position may be chosen according to the nature of the item to be inserted through the aperture of the puncturing device. The device may include a means providing a level of resistance to the movement of the puncturing elements. This is advantageous where for example the item to be inserted through the aperture is particularly heavy. Providing a level of resistance allows puncturing of the seal to be carried out relatively smoothly without any jarring of the item as it is inserted through the aperture or without any damage to the device.

As stated above, the puncturing elements may move from the first position to the second position by pivoting around the point of attachment of the puncturing elements to the member. Alternatively, the puncturing elements may be attached to the member by means which allow the puncturing elements to move to the second position without pivoting around an axis. For example, the inner surface of the member may comprise a channel engaging the first end of each puncturing element, the channel extending along the member in the direction of movement of the inserted item. The channel may exert sufficient resistance to the first end of each puncturing element to retain each puncturing element in the first position. When an item is inserted through the aperture of the puncturing device, it urges one, more or all of the puncturing elements to move along the channel in which the first end of each puncturing element is retained, thereby puncturing the puncturable material.

The means by which each puncturing element is attached to the member are such that the puncturing elements preferably remain attached to the member when in the first and second positions. Alternatively, each puncturing element may become detached from the member when moving from the first to the second position.

The puncturing elements may be shaped so as to easily puncture a puncturable material, thereby minimising the force required by the user to puncture the material. For example, the second end of each puncturing element may form a sharp point which is the first point of contact between the puncturing element and the puncturable material. Each puncturing element may comprise a sharpened lower surface capable of cutting (thereby puncturing) the puncturable material.

The upper surface (facing the item to be inserted through the aperture) and lower surface (opposite the upper surface) of each puncturing element may meet at the second end of each puncturing element to form a sharp point. The point may be closer to the puncturable material than an item to be inserted through the aperture when the item contacts the upper surface of the puncturing elements. This ensures that the puncturable material is punctured, and the material is removed from the path of the inserted item, before the item reaches the puncturable material.

Each puncturing element may include an upper projection defining the surface of contact between the puncturing element and the item to be inserted through the aperture of the puncturing device. Preferably, the upper projection presents a minimal surface area of contact with the inserted item. Where the inserted item carries a sample material thereon (e.g. where the inserted item is a swab or similar), this ensures that a minimal amount of sample material contacts the puncturing elements, and therefore reduces the potential for sample material to be adsorbed onto the puncturing elements.

Each puncturing element may include a lower projection which is positioned on the opposite side of the puncturing element to the upper projection and which is for puncturing the puncturable material. The lower projection may form a cutting edge. The lower projection may be separated from the upper projection by a distance sufficient to ensure that the puncturable material is punctured and is removed from the path of the item inserted into the aperture, before the item reaches the material.

In between the upper and lower projections, the width of the puncturing element may exceed the width at the upper and lower projections. This ensures that, after puncturing the puncturable material, the increased width of the puncturing element forcibly removes the material from the path of the inserted item. The inserted item is therefore brought into minimal contact with the puncturable material as the item passes through the aperture.

The puncturing device of the invention may comprise a single puncturing element, or may comprise a plurality of puncturing elements (for example, the puncturing device may contain 2, 3, 4, 5, 6, 7, 8, 9, 10, 11, 12, 13, 14, 15, 16, 17, 18, 19, 20 or more puncturing elements). Though the terms "a puncturing element" or "puncturing elements" or equivalent singular and plural terms may be used herein in relation to a specific embodiment of the puncturing device, it will be appreciated that any embodiment of the puncturing device defined herein may comprise either a single puncturing element or a plurality of puncturing elements.

The puncturing elements may be composed of any material of sufficient strength to puncture a puncturable material. For example, the puncturing elements may be composed of a material such as a plastic material, a metal or metal alloy, a ceramic or a non-metal. Examples of such are high density polyethylene, PVC, polypropylene, nylon, PTFE, stainless steel and titanium. The puncturing elements may be flexible, or may be rigid. When rigid, the puncturing elements may be movable relative to the member by means of, for example, a hinged attachment to the member. Alternatively, the puncturing elements may be composed of two or more materials, so that at least a portion of the second end of each puncturing element is rigid, and at least a portion of the first end of each puncturing element is flexible. The puncturing elements may therefore comprise a rigid second end, though may still be capable of pivoting around a point of attachment of the puncturing elements to the member because, at the point of attachment, the puncturing elements are formed of a flexible material.

Preferably, the puncturing elements are composed of a material whose flexibility varies according to the thickness of the material. For example, polyethylene is flexible when formed in a shape with a thin cross-section, though less flexible when formed in a shape with a thick cross-section. Thus, the puncturing elements may have a thin cross sectional area at, or close to, the point of attachment of the puncturing element to the member, to enable the second end of the puncturing elements to be deflected by an item inserted through the aperture of the puncturing device. The puncturing elements may have a thicker cross-sectional area along the body of the puncturing elements away from the point of attachment to the member, to ensure that the puncturing elements are sufficiently rigid to puncture the puncturable material.

Preferably, the puncturing elements are composed of high density polyethylene or polypropylene.

The puncturing elements may be composed of a material whose properties are selected according to a comparison with the properties of the item to be inserted through the aperture of the puncturing device. The puncturing elements may be composed of a suitably high strength material to resist damage to the puncturing elements when the item is inserted through the aperture of the device.

The puncturing elements may be manufactured as separate components which are subsequently attached to the member. Alternatively, the puncturing elements may be integral to the member. For example, the puncturing device of the invention may be formed from a plastic, and may be manufactured from a mould defining the entire puncturing device. The puncturing device may be manufacturing by any convenient method, such as by injection moulding.

The member of the puncturing device may form any shape. Similarly, the aperture defined by the member may be any shape.

The “insertion end” of the puncturing device defines the end of the member through which an item first passes when the item passes through the puncturing device. The “puncturing end” of the puncturing device defines the end of the member closest to a puncturable material which the device is intended to puncture. In one embodiment of the invention, the second end of each puncturing element is capable of moving towards either end of the puncturing device, and it is therefore immaterial which end of the puncturing device contacts a liquid container including a puncturable material. In those embodiments in which each puncturing element is only capable of moving towards one end of the member, this end will always be the “puncturing end” of the device, and this end must be located proximal to the puncturable material so that the puncturing elements are capable of puncturing the material.

In one embodiment, when the puncturing elements are in the first position, the second end of each puncturing element does not extend beyond the puncturing end of the device. Thus, for example, when a puncturing device of the invention is placed on a planar liquid-tight seal, the puncturing end of the device may be in contact with the liquid-tight seal, though the second end of each puncturing device will not be in contact with the liquid-tight seal. When an item is inserted through the aperture of the puncturing device, the puncturing elements are urged to move into contact with the liquid-tight seal and are urged to puncture the seal by the force applied to them via the inserted item. This embodiment reduces the likelihood of damage being sustained to the second end of the puncturing elements where the puncturing device is manufactured separately from the liquid container to which the puncturing device may be attached.

The item for insertion through a puncturing device of the invention may be any item which is desired to be inserted into a liquid container. For example, the item may be a conduit whose function is to transfer liquid from the liquid container to another destination. For example, the item may be a pipe or a straw. Thus, the puncturing device may be used on a drinks container. Alternatively, the item may be a device whose function is to transfer material contained on or in the item into a liquid container. For example, the item may be a swab.

In a seventh aspect, the present invention provides a puncturing device of the sixth aspect in combination with a liquid container having a liquid seal formed of a puncturable material.

The member of the puncturing device may be any shape according to the requirements of the liquid container to which the member is to be attached. For example, the member may be circular, square, pentagonal, hexagonal, heptagonal, octagonal or elliptical, or any other shape. The shape of the member may be designed to give a distinctive appearance to the puncturing device.

The aperture of the puncturing device may be any shape, and may be adapted according to the dimensions of the item to be inserted through the aperture. For example, the aperture may be circular, square, pentagonal, hexagonal, heptagonal, octagonal, elliptical, or any other shape.

The member may be capable of attachment to the liquid container in such a way that the puncturing elements can be moved from the first position (the position in which they do not contact the liquid seal present on the liquid container) to the second position (the position in which the puncturing elements contact and puncture the liquid seal present on the liquid container). Accordingly, the member may comprise means for attachment to the liquid container. The puncturing device may be attached to the liquid container by any suitable means. For example, where the liquid container is a cylinder comprising a liquid seal positioned across the width of one end of the cylinder, the member may be formed in the shape of a circular cap which is capable of being attached to the end of the cylinder having the liquid seal thereon. The member may be attached to the cylinder by a friction fit.

Alternatively, the member may comprise a thread which can engage with a corresponding thread on the liquid container, so that the puncturing device may be attached via a threaded screw-fit. Alternatively, separate attachment means may be used to attach the member to a liquid container. For example, screws, nails, tacks, adhesives, clips or other attachment means known in the art may be used. The member may also comprise protruding portions extending away from the aperture, which can be attached to the liquid container by any suitable means. The shape of such protruding portions may be adapted to conform to the shape of the liquid container to which the puncturing device is to be attached.

Preferably, the member is attached to a liquid container by a friction fit.

It will be appreciated by the skilled person that the exact dimensions of the member may be tailored according to the dimensions of the liquid container to which the member is to be attached.

The liquid container may comprise a plurality of liquid seals, each formed of a puncturable material. The puncturing device of the sixth aspect may puncture one or more of the liquid seals.

The liquid container may include a plurality of puncturable liquid seals and a puncturing means within the container, the puncturing means being capable of puncturing at least one of the liquid seals. In an eighth aspect, the invention provides such a liquid container. Preferably, the liquid container comprises first and second liquid seals provided at opposite ends of the liquid container, and a puncturing means within the container capable of puncturing the second liquid seal. The puncturing device of the sixth aspect may be attached to the liquid container so that it is capable of puncturing the first liquid seal.

The puncturing means within the container of the eighth aspect may be a puncturing device according to the sixth aspect of the invention, or may be an alternative puncturing means.

The puncturing means within the container may comprise one or more puncturing elements attached at a first end to the inside surface of the liquid container, each puncturing element extending into the cavity formed by the liquid container to form a second end of the puncturing element, the second end being movable in relation to the liquid container and capable of puncturing a liquid seal.

Each puncturing element may comprise an arm portion linking the first and second ends of the puncturing element. Alternatively, each puncturing element may comprise a plurality of arm portions emanating from the second end of the puncturing element and attaching to the inner surface of the liquid container at a first end of each arm portion. For example, the puncturing element may comprise two arm portions. The first end of the arm portions may attach to the inner surface of the liquid container at separate attachment points. Relative to a horizontal plane passing through the container at the point of attachment of one of the arm portions, the second (or each additional) arm portion of the same puncturing element may be attached to the inner surface of the liquid container in the same horizontal plane.

When an item is inserted into the liquid container through a first liquid seal, the item may be urged to move through the liquid container into contact with the puncturing means within the liquid container. A puncturing device of the sixth aspect may be used to ease the insertion of the item through the first liquid seal into the liquid container.

Where the first liquid seal is positioned at an upper end of the container and a second liquid seal is positioned at a lower end of the container, the liquid may be retained within the container by the force of gravity, and by the intact second liquid seal. The second liquid seal may be positioned in the container in alignment with the first liquid seal so that an elongate item inserted into the container through the first liquid seal will contact the puncturing means proximal to the second liquid seal as the item is inserted further into the container.

The inserted item may urge the puncturing element of the puncturing means within the container to move from a first position (in which the puncturing element does not contact the second liquid seal) to a second position in which the second liquid seal is contacted and punctured by the puncturing element. The movement of the puncturing element from the first to the second position causes the puncturing element to puncture the second liquid seal. The puncturing element may also remove the material of the liquid seal from the path of the item as the item is inserted through an opening of the container previously covered by the second liquid seal. Where the puncturing device comprises a puncturing element with two arm portions as described above, the potential for lateral movement of the puncturing element when the item is further inserted into the container is reduced because of the attachment of the two arm portions to the liquid container. The two arm portions therefore allow greater control of the direction of movement of the puncturing element when moving from the first position to the second position. Once the second liquid seal is punctured, liquid is able to exit the liquid container via the opening previously covered by the second liquid seal.

The second end of the one or more puncturing elements may form a conical shape with a sharp point facing a liquid seal in the container, and a flat base of the conical shape facing an item inserted into the container.

Alternative liquid containers to which a puncturing device of the sixth aspect may be attached are described as follows. The container may comprise a first liquid seal located at the top of the container and a second liquid seal located opposite the first liquid seal, at the bottom of the container. The container may comprise two portions; an upper portion proximal to the first liquid seal, and a lower portion proximal to the second liquid seal. The upper portion may be defined by a volume which is greater than the lower portion. Where the container has a generally cylindrical shape, the lower portion may have a diameter which is marginally greater than the largest diameter of an item (such as a sampling device) to be inserted into the container. The lower portion may taper outwardly towards the base of the container. The upper portion may have a diameter which is greater than the diameter of the lower portion. The inner walls of the upper portion may taper inwardly towards the narrower diameter of the lower portion. Thus, when a sampling device is inserted through the first seal into the liquid container, the sampling device enters the upper portion of the container. As the sampling device is further advanced into the lower portion of the container, liquid present in the lower portion of the container is displaced upwards around the sampling device, into the upper portion. The reduced diameter of the lower portion therefore ensures that contact between the sampling device (and any sample thereon) and the liquid is maximised. This displacement of liquid can be achieved by adapting the volumes of the upper and lower portions of a container of any shape (not necessarily cylindrical). The sampling device may be further advanced into the liquid container to contact and puncture the second liquid seal. Liquid then flows from the upper portion of the container into the lower portion around the sampling device, and out of the container through the punctured second seal. The second seal may be punctured by the item, or by a puncturing means, for example a puncturing device of the sixth aspect.

The liquid container may further comprise flange portions to which the one or more puncturable liquid seals are attached. For example, the container may comprise upper and lower flanges to which the first and second seals are attached, respectively.

The liquid seals may be formed of any inert puncturable material suitable for retaining liquid within the container. The liquid seals may be, for example, non-porous films or metallic seals (e.g. aluminium foil). Suitable materials for the manufacture of non-porous films include thermoplastic polymers, such as polyolefins (e.g., polyethylene, polypropylene, etc.), including homopolymers, copolymers, terpolymers and blends thereof; ethylene vinyl acetate; ethylene ethyl acrylate; ethylene acrylic acid; ethylene methyl acrylate; ethylene normal butyl acrylate; polyurethane; poly(ether-ester); poly (amid-ether) block copolymers, and other similar materials.

The thickness of the seal material may be varied to alter the strength and permeability of the seal. When the seal is composed of aluminium foil, suitable thicknesses for retaining liquid within the container may range from about 15 to about 50 microns, preferably from about 20 to about 30 microns.

Preferably, the liquid container of the eighth aspect is manufactured by an injection moulding process. Preferably, the liquid container is composed of high density polyethylene.

The liquid container may comprise one or more deflectable protrusions extending into the inner space of the container from the inner side walls of the container. In a ninth aspect, the invention provides a container comprising a plurality of deflectable protrusions extending into the inner space of the liquid container from the inner side walls of the container. These protrusions brush against a sampling device inserted into the container, thereby disturbing a sample present on the sampling device and assisting in the transfer of the sample from the sampling device to the liquid.

The protrusions are attached at a first end to an inner wall of the container, each protrusion comprising a second end extending into the inner space of the container. The protrusions may extend at any distance into the inner space of the liquid container. For example, the protrusions may be spaced around the inner circumference of the container and may each extend at a uniform length towards the middle of the liquid container, thereby defining an aperture through the protrusions in the middle of the container. The protrusions may be shaped as elongate "fingers" with a uniform breadth along the elongated shaft of each finger. Alternatively, the breadth of each protrusion may vary along the length of the protrusion. For example, the breadth of each protrusion may be greater at the point of attachment to the inner side wall of the container than at the tip of the protrusion. Thus, the protrusion may taper inwardly from the base, to a point at the tip of the protrusion. Alternatively, the protrusions may taper outwardly towards the tip of the protrusion.

The protrusions may extend into the container perpendicularly to the inner walls of the container. Alternatively, the protrusions may extend into the container at an angle other than 90° to the walls of the container. For example, the protrusions may extend upwardly into the inner space of the container at an angle in the range of from 1° to 90° to the walls of the container. This may enhance the disturbance of sample material from a sampling device, thereby transferring more sample material from the sampling device to the liquid. The protrusions are deflected by the sampling device entering the liquid chamber in a similar manner as the puncturing elements described above are moved from the first to the second position. The protrusions can be composed of any of the materials described above as being suitable for composing the puncturing elements. The protrusions can be attached to the inner side walls of the container by a hinge mechanism, or may be integral with the liquid container. Preferably, the protrusions are integral with the container. Preferably, the protrusions are formed of a flexible material. The protrusions preferably have an area with a thin cross section immediately adjacent the point of attachment to the container, and a thicker cross section throughout the rest of the protrusion. This allows the protrusions to bend at the area having a thin cross section as a sampling device contacts the protrusions.

The protrusions are preferably attached to the container in the same horizontal plane around the inner circumference of the container, thereby forming a "ring" of protrusions. Alternatively, the protrusions may be attached at different horizontal planes through the container, or along the entire length of the inner surface of the container. When the container comprises an upper portion and a lower portion of lesser volume as described above, the ring of protrusions is preferably positioned at the top of the lower portion.

The container of the ninth aspect may also include a puncturing means within the container, the puncturing means being capable of puncturing a liquid seal present in the container. Thus, the container of the ninth aspect may include the features of the container of the eighth aspect.

Exemplification

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified. The drawings illustrate exemplary embodiments of the invention only, and should not be viewed as limiting the scope of the invention.

FIG. 1 illustrates a puncturing device of the invention comprising a member 2 and three puncturing elements 3, 3', 3". Each puncturing element comprises an arm portion 8 attached at a first end to the upper edge of the member 2 and extends radially towards the centre of the aperture defined by the member 2. Extending perpendicularly from each arm 8 is an upper projection 6 and a lower projection 7. The upper projection 6 provides a minimal surface of contact to an item to be inserted through the device. The lower projection 7 comprises a sharpened cutting surface capable of cutting (thereby puncturing) a liquid seal. The arm 8 is flexible so that it can move downwardly when a force is applied to the upper projection 6.

Figure 2:
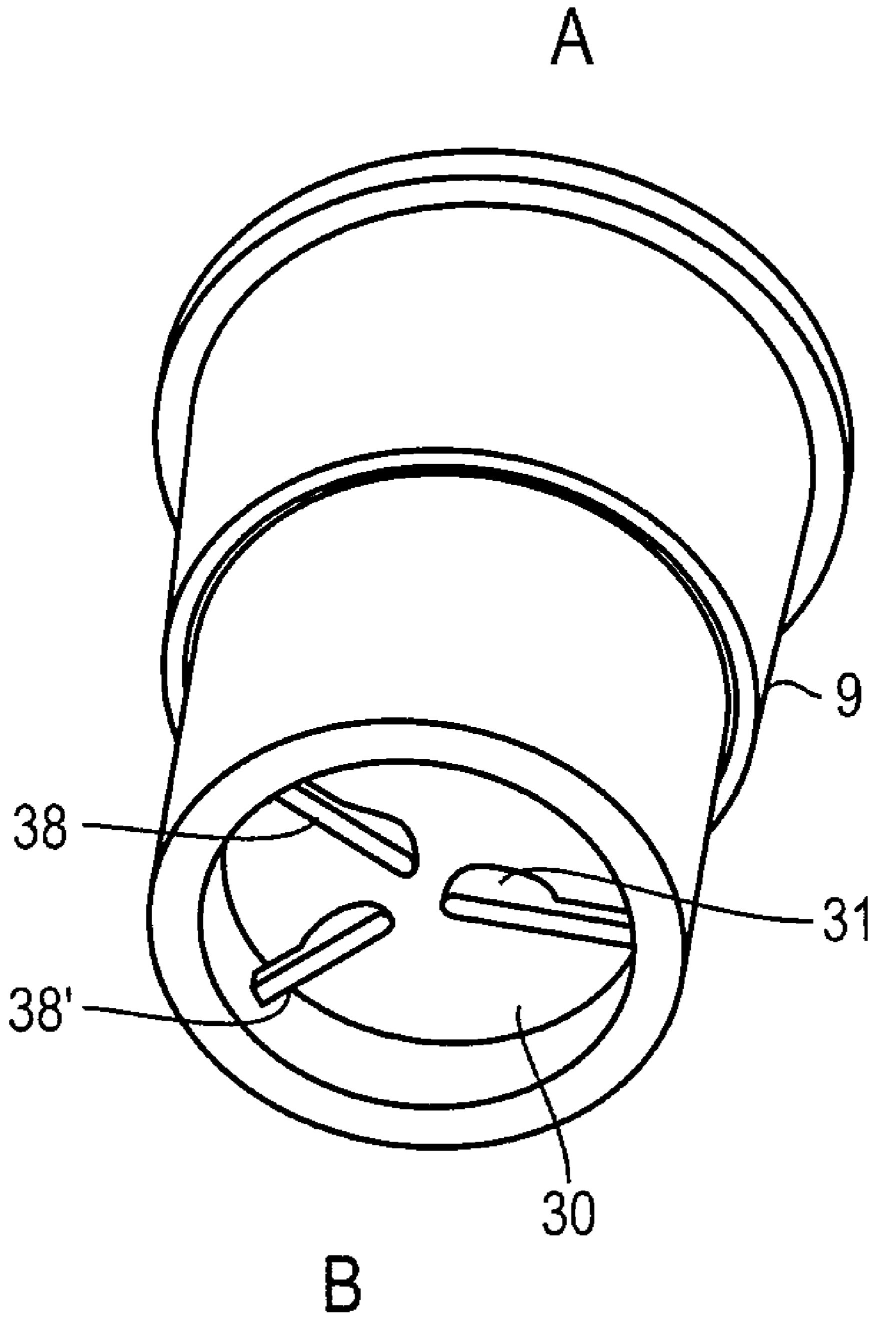
FIG. 2 shows a perspective view of a liquid container according to the eighth aspect of the present invention.

FIG. 2 shows a liquid container 9 according to the eighth aspect of the invention, comprising a puncturing means 30 within the liquid container 9 towards the base of the container 9. The puncturing means 30 comprises a conical second end 31 with a sharp point capable of puncturing a second liquid seal (not shown) sealing the base of the liquid container 9. The puncturing means 30 comprises two arm portions 38, 38' attached to the inner surface of the liquid container 9. In use, an item is inserted into the liquid container at end A so that the item abuts the puncturing means 30 and forces the conical end 31 to move towards and puncture a puncturable liquid seal (not shown) sealing the base of the container at end B. During such movement, the puncturing means 30 pivots about the point of attachment of the arms 38, 38' to the container.

Figure 3A:
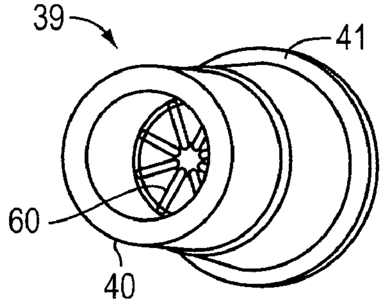
FIG. 3*a* shows a perspective view of the underside of a liquid container of the ninth aspect of the invention.
Figure 3B:
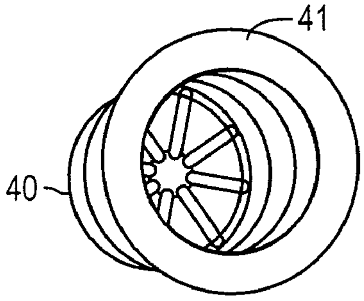
FIG. 3*b* shows a perspective view of the upper side of a liquid container of the ninth aspect of the invention.
Figure 3C:
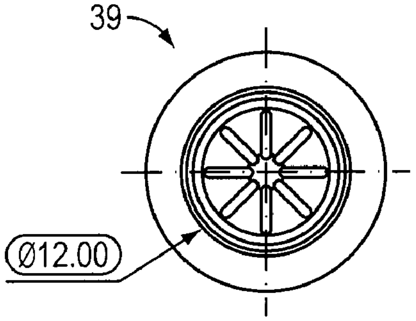
FIG. 3*c* shows a top view of a liquid container of the ninth aspect of the invention.

FIGS. 3*a* and 3*b* show underside, and upper side views of a liquid container 39 of the ninth aspect of the invention, respectively. The container contains an upper flange 41 and a lower flange 40 to which a first and second liquid seal can be attached, respectively. The container comprises deflectable protrusions 60 which extend radially into the centre of the container. FIG. 3*c* shows a top view of the container 39, wherein the diameter of the inside of the upper portion of the container at a cross section taken at the top of the upper portion is 12 mm.

Figure 4A:
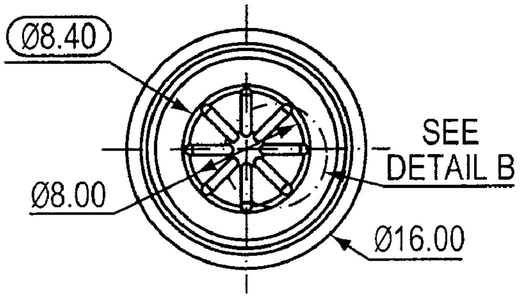
FIG. 4*a* shows a top view of a liquid container of the ninth aspect of the invention.
Figure 4B:
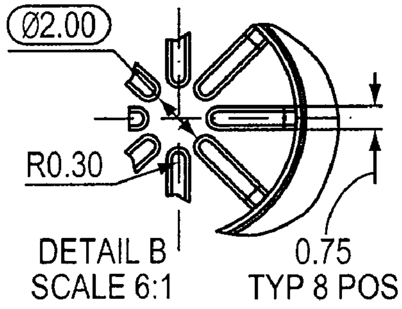
FIG. 4*b* shows in detail the arrangement of deflectable protrusions in the area B outlined in FIG. 4*a*.

FIG. 4*a* shows a top view of a container 39 of the ninth aspect of the invention, wherein the diameter of the outer surface of the upper flange is 16 mm, the diameter of the inside of a lower portion of the container is 8 mm at a cross section taken at the top of the lower portion, and the diameter at a cross section taken at the base of the lower portion is 8.4 mm. Thus, the inner walls of the lower portion taper outwardly towards the base of the container. The upper and lower portions of the container 39 are shown in FIG. 5. The breadth of each of the protrusions shown in greater detail in FIG. 4*b* is 0.75 mm. The protrusions define a generally circular aperture in the middle of the container. The diameter of the aperture is 2 mm.

Figure 5A:
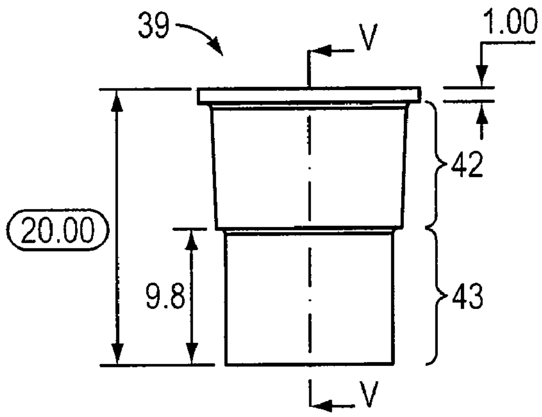
FIG. 5*a* shows a side view of a liquid container of the ninth aspect of the invention.
Figure 5B:
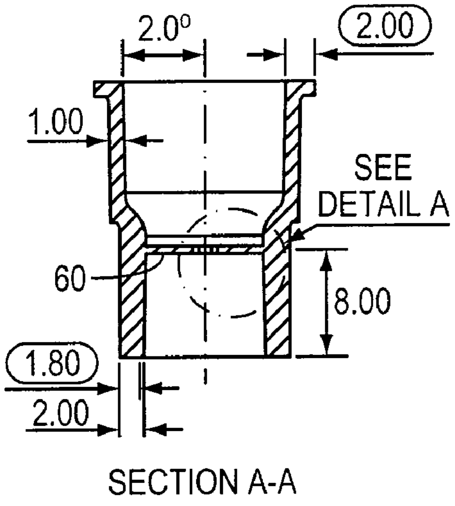
FIG. 5*b* shows a cross section through the line V-V in FIG. 5*a*.
Figure 5C:
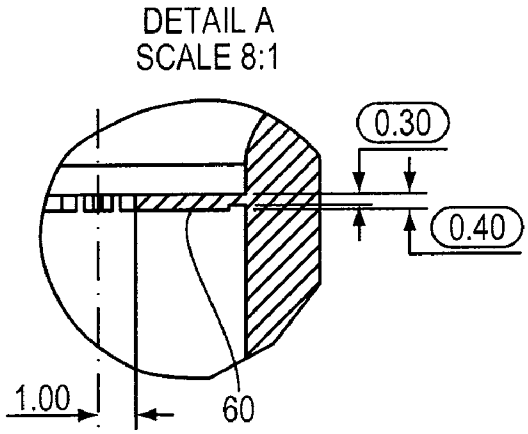
FIG. 5*c* shows in detail the arrangement of deflectable protrusions in the area A outlined in FIG. 5*b*.

FIG. 5*a* shows a side view of a container 39 of the ninth aspect of the invention, showing an upper portion 42 of greater diameter than the lower portion 43. The total height of the container is 20 mm. The height of the lower portion 43 is 9.8 mm. The height of the upper flange portion is 1 mm. FIG. 5*b* shows a cross section of the container 39 taken through the line V-V in FIG. 5*a*. The distance from the bottom of the container to the upper edge of the protrusions 60 is 8 mm. In FIG. 5*b* it can be seen that the upper portion 42 has a greater internal volume than the lower portion 43, and that the inner walls of the upper portion taper inwardly in a curve towards the lower portion. The deflectable protrusions 60 form a ring around the top of the lower portion 43. FIG. 5*c* shows in detail the attachment of the deflectable protrusions 60 to the side wall of the container 39. The deflectable protrusions are integral with the container 39, and comprise an area of reduced thickness close to the point of attachment to the container. This area of reduced thickness allows the deflectable protrusions to bend, when deflected by an item inserted into the container 39. The area of reduced thickness in the example illustrated in FIG. 5*c* is 0.3 mm, compared to a cross sectional thickness of 0.4 mm throughout the remainder of the protrusions. The container illustrated in FIGS. 3-5 can also comprise the features of the container illustrated in FIG. 2, and vice versa. Thus, the container of the eighth aspect can include any of the features of the ninth aspect.

Figure 6:
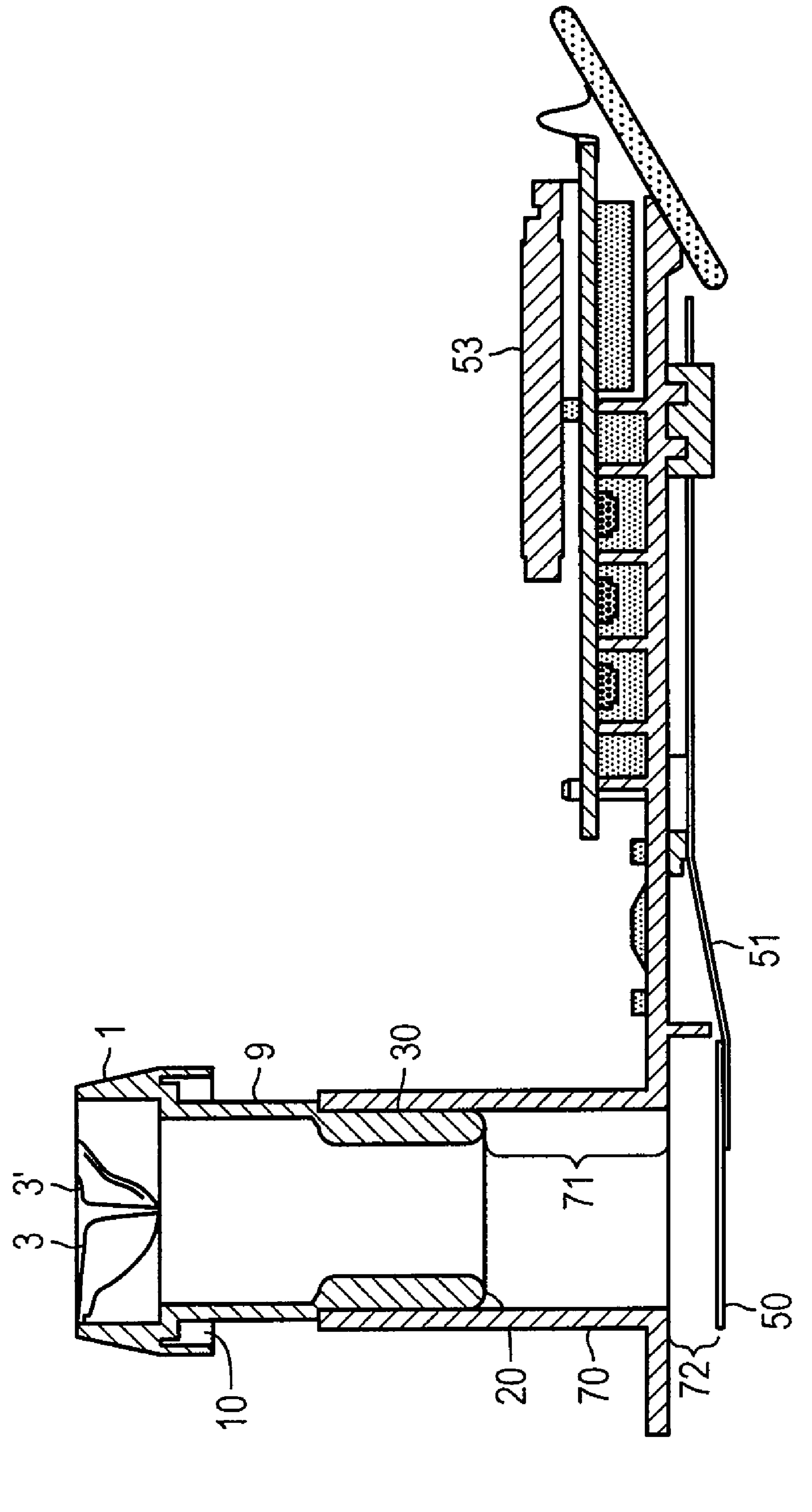
FIG. 6 shows a side view in cross section of a puncturing device of the invention located in an assay device of the invention.

FIG. 6 illustrates an assay device in which the puncturing device 1 is attached to a liquid container 9 of the eighth aspect. The assay device can also include a container of the ninth aspect, or a container combining the features of the eighth and ninth aspects. The liquid container 9 comprises a first liquid seal 10 and a second liquid seal 20. The puncturing device 1 is located so that the lower projection 7 of each puncturing element 3, 3' does not contact the first liquid seal 10 when the puncturing elements are in a first position.

In use, an item (preferably a sampling device such as a swab) is inserted through the puncturing device 1, contacting the upper projection 6 of each puncturing element 3, 3' and forcing the puncturing elements to move downwards, towards the position of a liquid seal located below the puncturing elements. The lower projection 7 of each puncturing element 3, 3' punctures the liquid seal, and as the puncturing elements 3, 3', are progressively moved downwards, pivoting around the point of attachment to the member (and thereby arcing towards the side of the container 9), the arm portion 8 urges the material of the seal away from the centre of the aperture, thereby reducing the potential for the inserted item to contact the material of the seal as the item passes through the device 1.

When the sampling device has been inserted into the liquid container 9, the sample contained on the sampling device contacts the liquid within the liquid container 9. The sampling device is then further inserted into the liquid container 9, towards the second liquid seal 20. The sampling device contacts a puncturing means 30 and urges the puncturing means 30 to contact and puncture the second liquid seal 20.

Additionally, the assay device comprises a spacing element 70 which holds the liquid container 9 in an elevated position relative to a liquid receiver 50. The spacing element creates a space 71 between the second liquid seal 20 and the liquid receiver 50. This space 71 is preferably large enough to house the entire head of a sampling device inserted into the assay device, thereby allowing the entire head of the sampling device to pass through the liquid container 9. The dimensions of the spacer element 70 may be adapted so that the sampling device, when fully inserted into the assay device, does not contact the liquid receiver 50. Alternatively, the fully inserted sampling device may directly contact the liquid receiver 50. Contact between the sampling device and the liquid receiver 50 may enhance liquid transfer to the liquid receiver and a lateral flow carrier 51. When the sampling device comprises a shaft whose diameter is less than the greatest diameter of the head of the sampling device, insertion of the entire sampling head through the seal 20 and into the space 72 ensures that all of the liquid present in the container 9 is able to flow out of the container 9 and onto the liquid receiver 50. Thus, liquid is not trapped in the container 9 by occlusion of the lower portion of the container by the head of the sampling device. Also illustrated in FIG. 6 is an optional gap 72 between the base of the spacing element 71 and the liquid receiver 50.

Upon puncturing of the second liquid seal 20, liquid flows from the container 9 through the space 71 and gap 72 to a liquid receiver 50. The liquid then flows from the liquid receiver 50 to a lateral flow carrier 51, and along the lateral flow carrier 51 towards a detecting means 53.

Figure 7:
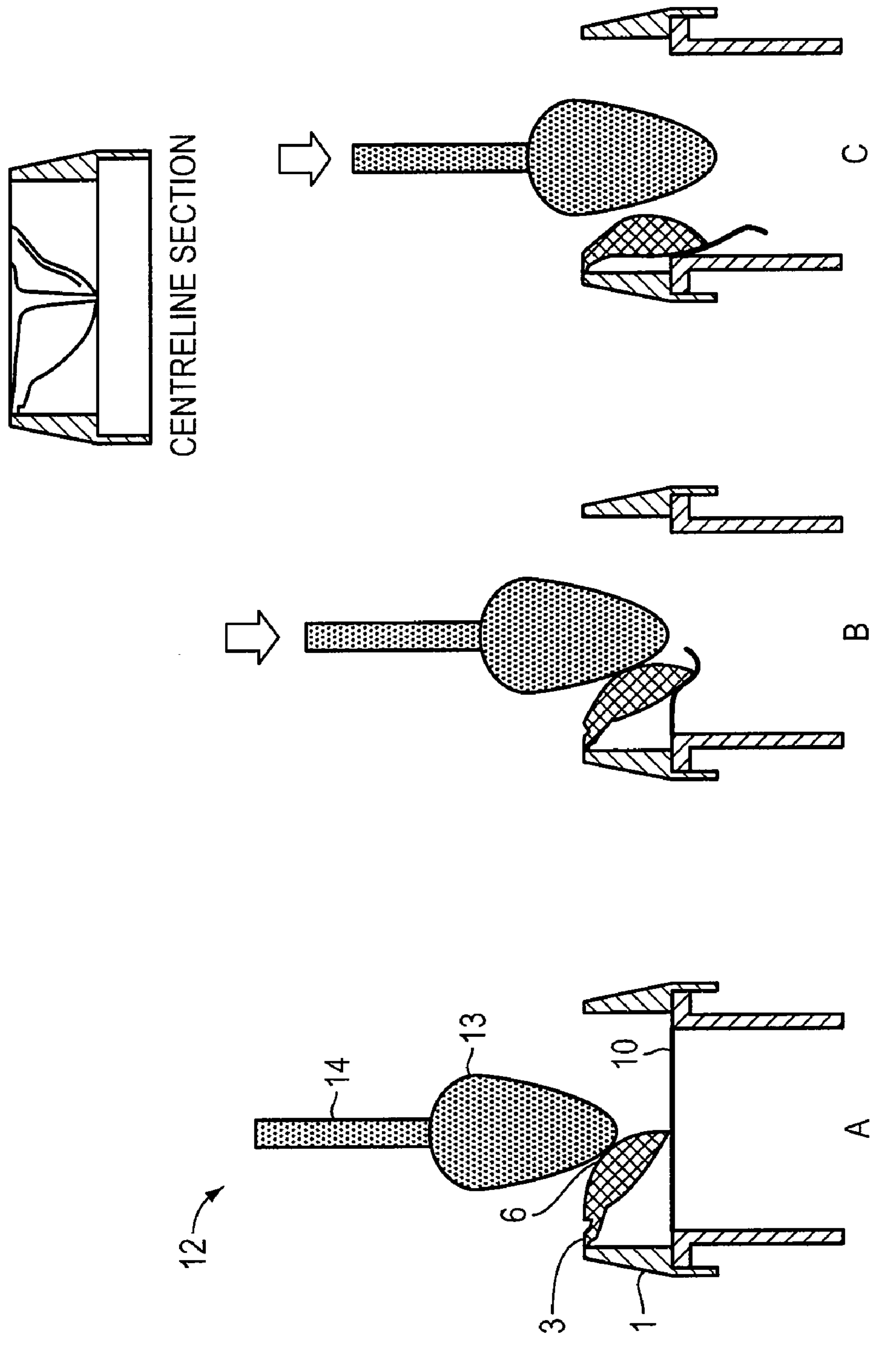
FIG. 7 shows a series of images illustrating the progressive advancement of an item through a puncturing device of the invention, in cross section.

FIG. 7 illustrates the action of the puncturing device 1 as a sampling device 12 comprising a head portion 13 and an elongate shaft 14 is inserted through the puncturing device 1. In FIG. 7A, the sampling device is inserted into the puncturing device so that the head portion contacts an upper projection 6 of a puncturing element 3 (only one puncturing element is shown, for clarity). The puncturing element 3 is shown in a first position. In FIG. 7B, the sampling device 12 is shown inserted further through the puncturing device 1, so that the puncturing element 3 is moved to a second position, thereby puncturing a liquid seal 10. FIG. 7C shows the sampling device 12 in a further advanced position, entering the liquid container. The puncturing element 3 is shown in a further advanced second position, with the material of the liquid seal 10 removed from the path of the sampling device 12 as it passes into the liquid container.

Figure 8:
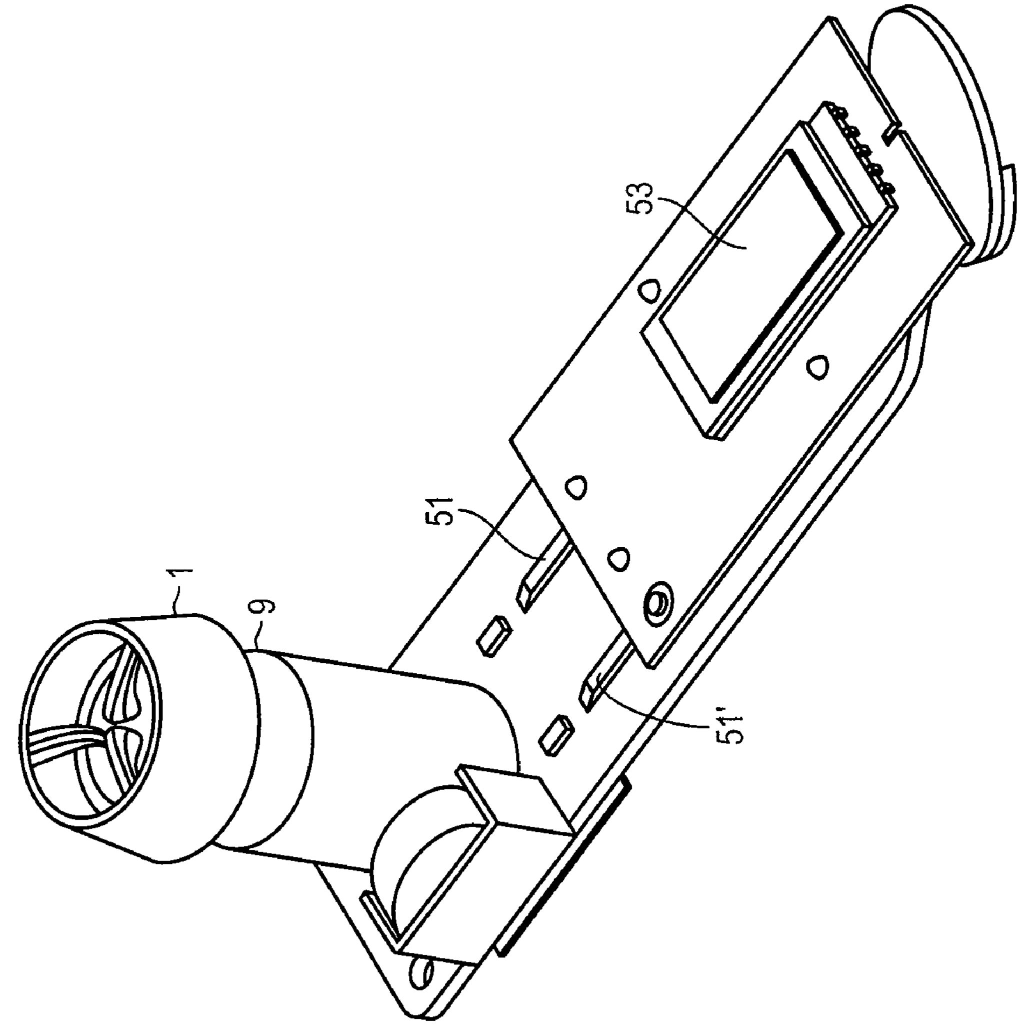
FIG. 8 shows an elevated view of a puncturing device of the invention located in an assay device of the invention.

FIG. 8 shows an elevated view of an assay device of the invention, comprising the puncturing device 1 positioned on a liquid container 9 of the eighth aspect. The assay device further comprises two lateral flow carrier strips 51, 51' capable of receiving liquid from the liquid container 9. The assay device further comprises a means 53 for detecting the presence of an analyte of interest in a sample.

Figure 9:
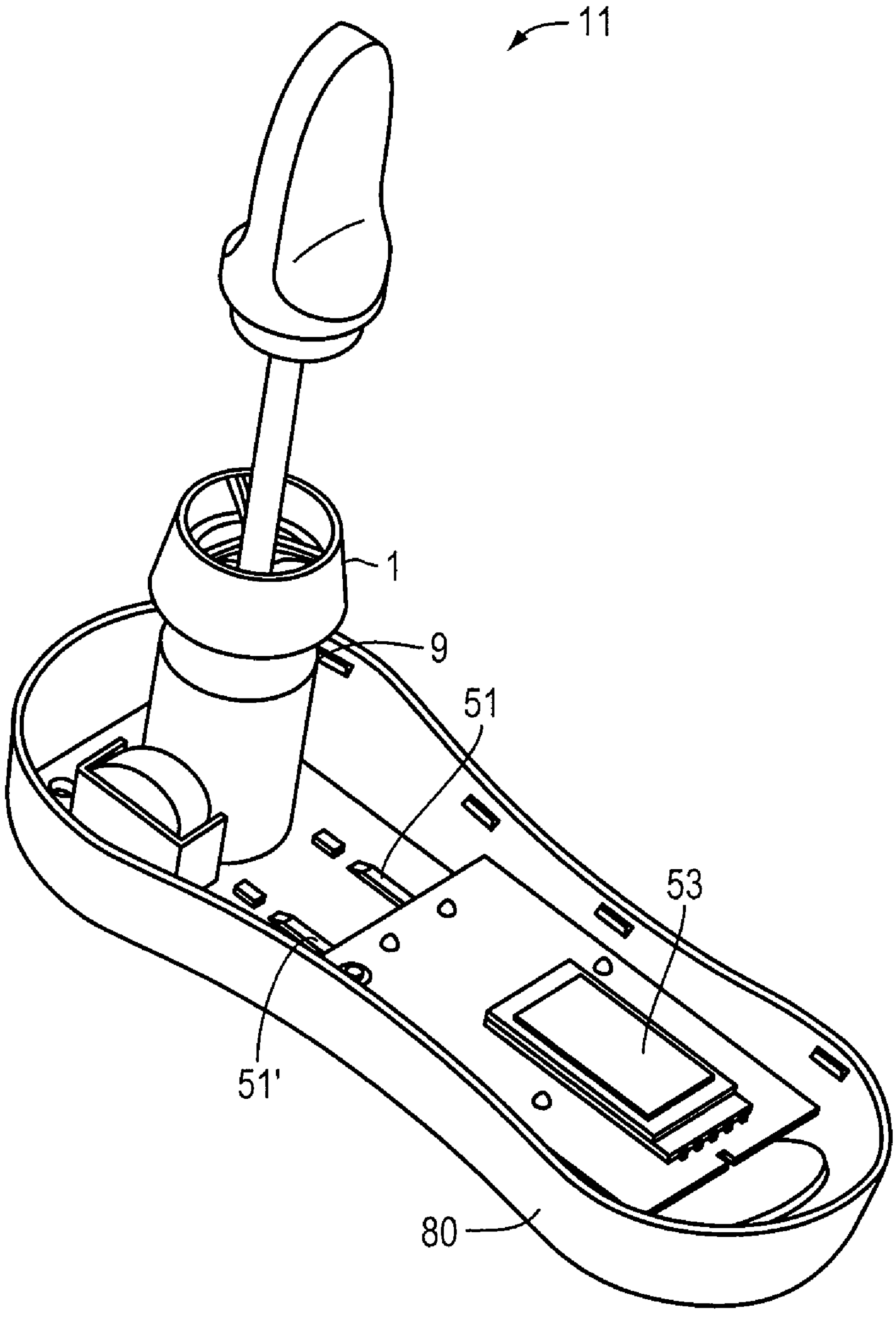
FIG. 9 shows an elevated view of a sampling device inserted through a puncturing device of the invention, which is located in an assay device of the invention.

FIG. 9 shows an elevated view of an assay device of the invention, comprising a sampling device 11 inserted through the puncturing device 1 into the liquid container 9. A lower casing 80 housing the assay device is also shown.

Figure 10:
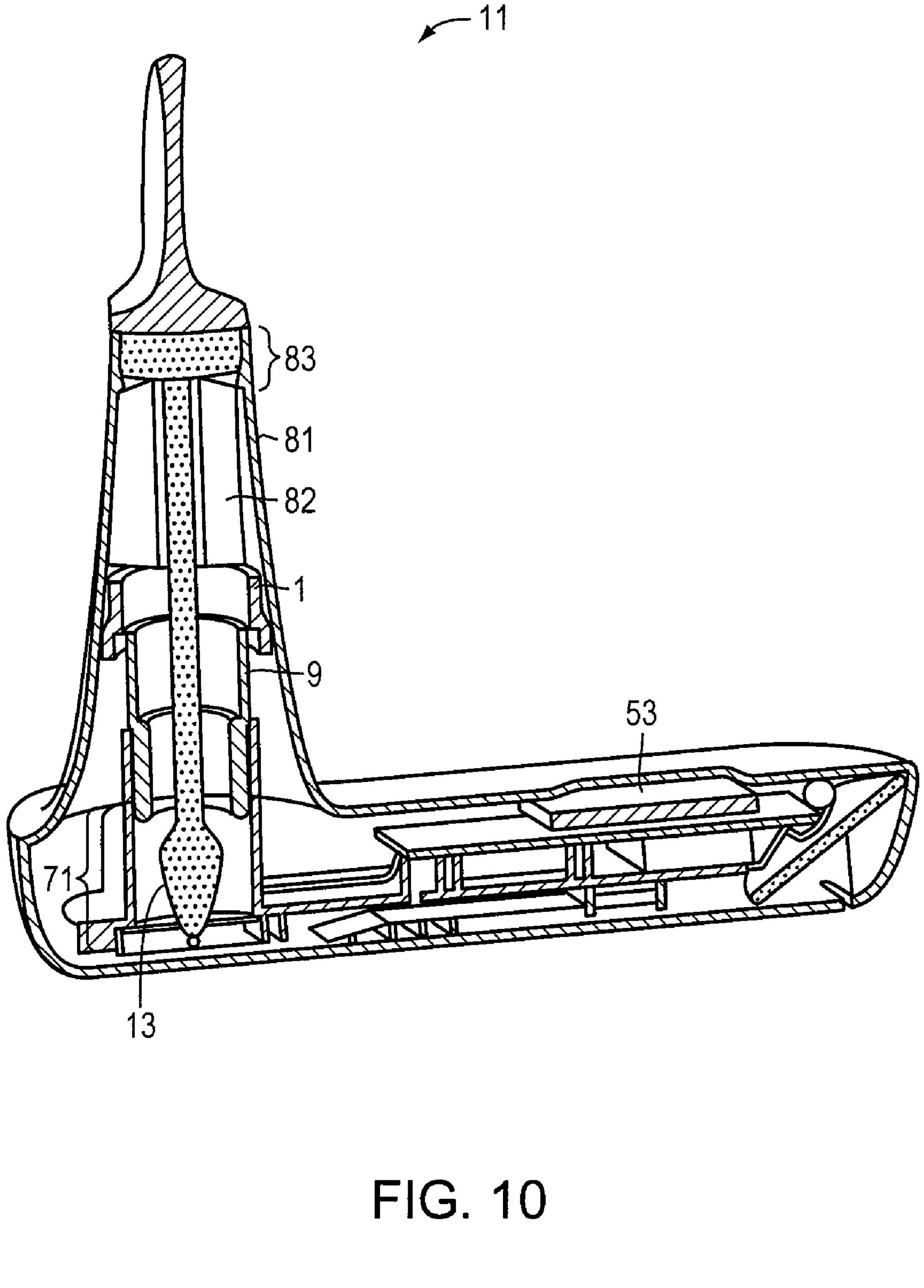
FIG. 10 shows a cross section of an assay device of the invention, with a sampling device inserted into the assay device.

FIG. 10 shows a cross section of an assay device of the invention, with a sampling device 11 inserted into the assay device. A neck portion 81 of the assay device is shown surrounding the puncturing device 1 and the liquid container 9, and extending vertically therefrom. The top of the neck portion provides an engaging means 83 capable of releasably engaging the sampling device 11. The sampling device may engage with the neck portion by any suitable engaging means known to the person skilled in the art. For example, the head portion of the sampling device may comprise a radial protrusion which clips into a mating recess in the top of the neck portion. Alternatively, the radial protrusion may be present in the top of the neck portion, and the recess present in the sampling device. Alternatively, the sampling device may comprise a protruding threaded portion which can engage a cooperating protruding thread present in the neck portion (thereby engaging by a mating screw fit). Preferably, the sampling device engages with the neck portion by a means which does not require rotating the sampling device or the neck portion. The engaging means serves to ensure that the sampling device is inserted into the liquid container to the correct depth, the engaging means serving to prevent the sampling device from being inserted any further into the container.

The neck portion 81 further comprises fin portions 82 which guide the sampling device towards the aperture of the puncturing device 1 as the sampling device is inserted into the assay device. The fin portions 82 may contact the puncturing elements of the puncturing device 1. The length of the neck portion can be adapted in accordance with the length of the sampling device so that, when the sampling device engages the neck portion at the engaging means 83, the head 13 of the sampling device 11 is located in the space 71 of the assay device.

Figure 11:
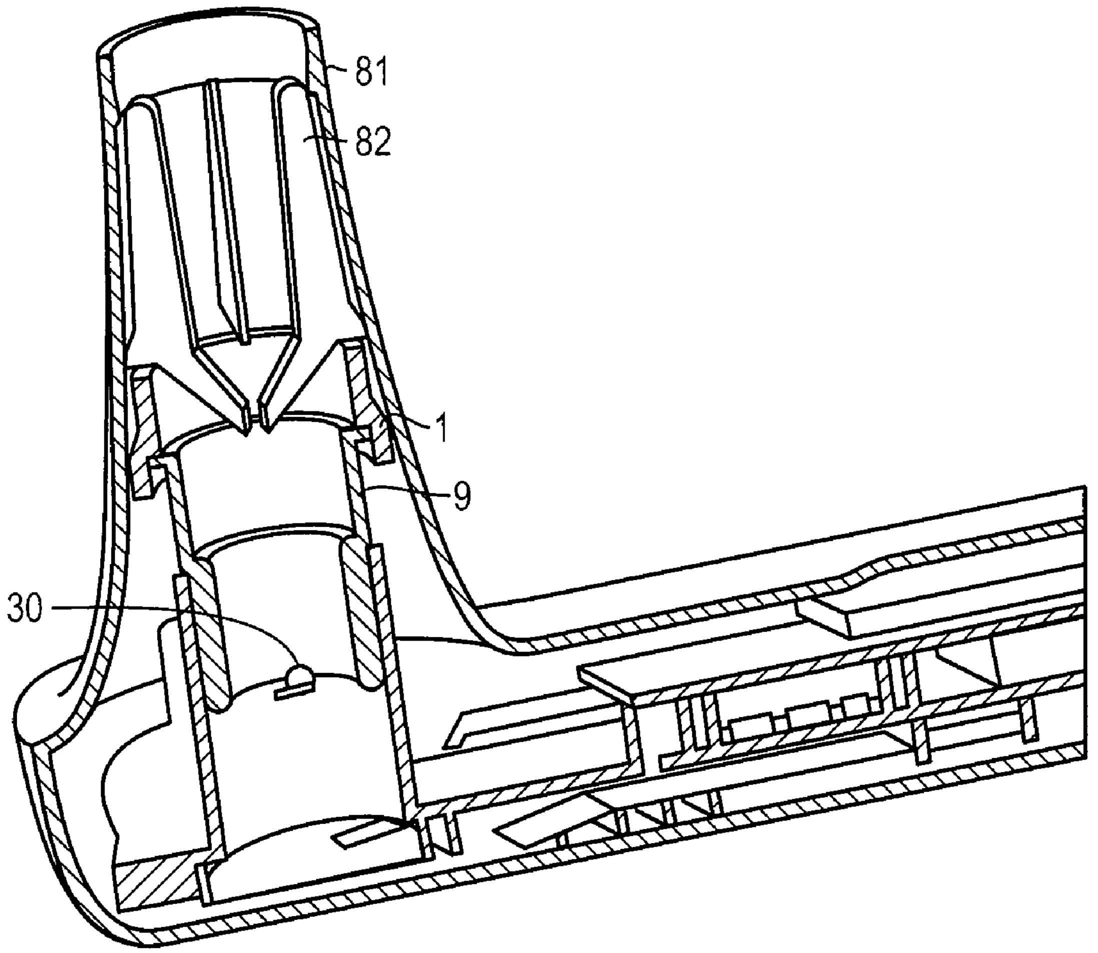
FIG. 11 shows a cross section of an assay device of the invention, without an inserted sampling device.

FIG. 11 shows, in perspective view, a cross section of an assay device of the invention without an inserted sampling device. The fin portions 82 are shown extending into the bore of the neck portion. The fin portions 82 extend along the vertical length of the neck portion, thereby acting as guiding runners which channel the sampling device towards the aperture of the puncturing device 1. The fin portions 82 may extend progressively further into the bore of the neck portion from the top of the neck portion to the puncturing device 1.

Figure 12:
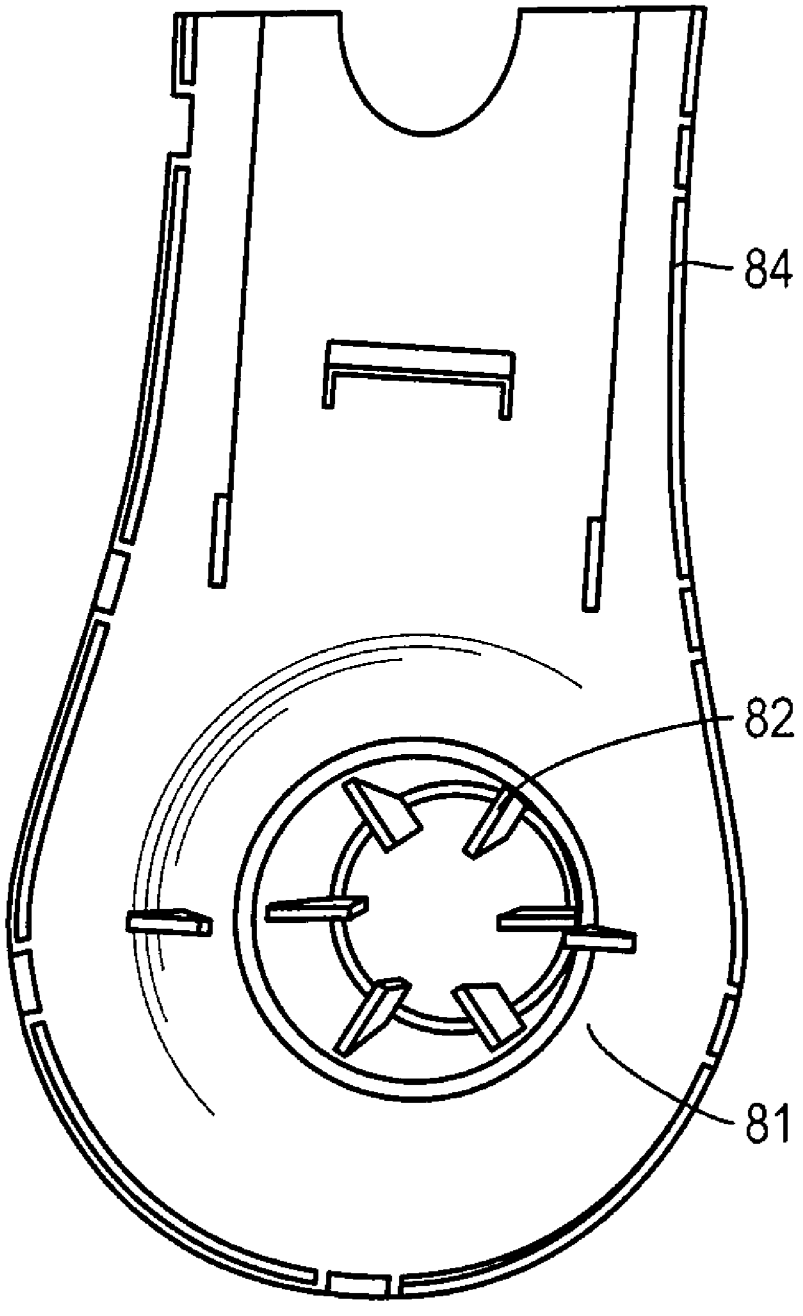
FIG. 12 shows an underside view of a neck portion of an assay device of the invention, with fin portions extending into the bore of the neck portion.

FIG. 12 shows an underside view of an upper casing 84 of an assay device of the invention. Fin portions 82 are shown extending into the bore of the neck portion.

Equivalents

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

References

All publications and patents mentioned herein are hereby incorporated by reference in their entirety as if each individual publication or patent was specifically and individually indicated to be incorporated by reference. In case of conflict, the present application, including any definitions herein, will control.

The invention claimed is:

1. An assay device for determining the presence and/or amount of an analyte of interest in a sample, the assay device comprising:

a sampling device, the sampling device comprising at least one puncturing element for opening a puncturable liquid seal;

a housing for receiving the sampling device, the housing comprising a neck portion, a liquid container portion, and an assay means;

wherein the liquid container comprises a first puncturable liquid seal and a second puncturable liquid seal, wherein the second puncturable liquid seal fluidically separates the liquid container from the assay means; and wherein the sample contacts the assay device when the second puncturable liquid seal is punctured by the sampling device.

2. The assay device according to claim 1, wherein the liquid container comprises a single liquid chamber.

3. The assay device according to claim 1, wherein the liquid pathway comprises a porous flow through matrix, wherein the porous flow through matrix comprises a lateral flow carrier.

4. The assay device according to claim 3, wherein the lateral flow carrier comprises a plurality of porous materials.

5. The assay device according to claim 1, wherein the neck portion comprises one or more projections extending into the bore of the neck portion.

6. The assay device according to claim 5, wherein the one or more projections are one or more fins.

* * * * *